(12) United States Patent
El Guindi et al.

(10) Patent No.: US 11,701,057 B1
(45) Date of Patent: Jul. 18, 2023

(54) HEARING DEVICE, HEARING DEVICE-BASED SYSTEMS AND METHODS FOR DETERMINING A QUALITY METRIC FOR AN OPTICAL MEASUREMENT

(71) Applicant: SONOVA AG, Staefa (CH)

(72) Inventors: Nadim El Guindi, Zürich (CH); Nina Stumpf, Maennedorf (CH); Niklas Ignasiak, Zürich (CH); Anna M. Parker, Basel (CH); Nicholas Ohs, Zürich (CH); Manuela Feilner, Egg b. Zürich (CH); Hans-Ueli Roeck, Hombrechtikon (CH)

(73) Assignee: Sonova AG, Staefa (CH)

( * ) Notice: Subject to any disclaimer, the term of this patent is extended or adjusted under 35 U.S.C. 154(b) by 0 days.

(21) Appl. No.: 17/674,635

(22) Filed: Feb. 17, 2022

(51) Int. Cl.
*A61B 5/00* (2006.01)
*H04R 25/00* (2006.01)

(52) U.S. Cl.
CPC .......... *A61B 5/6817* (2013.01); *A61B 5/0059* (2013.01); *H04R 25/305* (2013.01); *H04R 25/505* (2013.01); *H04R 25/604* (2013.01); *H04R 25/609* (2019.05); *H04R 2225/025* (2013.01)

(58) Field of Classification Search
None
See application file for complete search history.

(56) References Cited

U.S. PATENT DOCUMENTS

| 8,005,248 | B1 | 8/2011 | Davant |
| 10,257,602 | B2 | 4/2019 | Kofman |
| 2021/0185463 | A1 | 6/2021 | Kuipers et al. |
| 2021/0401311 | A1* | 12/2021 | Barnacka ............. A61B 5/6803 |

FOREIGN PATENT DOCUMENTS

| WO | WO-2020192956 A1 * | 10/2020 | ........... A61B 5/0084 |
| WO | WO-2022026337 A1 * | 2/2022 | ........... H04R 25/305 |

* cited by examiner

*Primary Examiner* — Kenny H Truong
(74) *Attorney, Agent, or Firm* — ALG Intellectual Property, LLC (57) ABSTRACT

An illustrative hearing system may be configured to cause an emitting device included in a hearing device to emit an output signal while the hearing device is at least partially positioned within an ear canal of a user and cause a sensor positioned outside the ear canal to attempt to detect the output signal. The sensor may be configured to output sensor data representative of one or more signals detected by the sensor during a time period corresponding to the emitting of the output signal by the emitting device. The hearing system may further be configured to determine, based on the sensor data, a quality metric for an optical measurement performed or to be performed by an optical measurement device included in the hearing device.

20 Claims, 6 Drawing Sheets

HEARING DEVICE, HEARING DEVICE-BASED SYSTEMS AND METHODS FOR DETERMINING A QUALITY METRIC FOR AN OPTICAL MEASUREMENT

BACKGROUND INFORMATION

A hearing device may enable or enhance hearing by a user wearing the hearing device by providing audio content received by the hearing device to the user. For example, a hearing aid may provide an amplified version of the audio content to the user to enhance hearing by the user. A hearing aid may further provide audio content to the user based on an audio stream (e.g., an electrical audio signal) received by the hearing device from a streaming source (e.g. a table microphone or a streaming service). As another example, a sound processor included in a cochlear implant system may provide electrical stimulation representative of the audio content to the user to enable hearing by the user.

In some cases, a hearing device may include an optical measurement device configured to perform an optical measurement of a user condition (e.g., heart rate, blood pressure, etc.) while the user is wearing the hearing device. Unfortunately, in some instances, motion and/or posture of the user wearing the hearing device may displace the hearing device on the user or the hearing device is not properly placed by the user, which may affect or degrade the accuracy of the optical measurement performed by the optical measurement device.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

An illustrative hearing system may be configured to determine a quality metric for an optical measurement performed or to be performed by an optical measurement device included in a hearing device configured to be worn by a user.

For example, the hearing system may be configured to cause an emitting device included in a hearing device to emit an output signal while the hearing device is at least partially positioned within an ear canal of a user; cause a sensor positioned outside the ear canal to attempt to detect the output signal, the sensor configured to output sensor data representative of one or more signals detected by the sensor during a time period corresponding to the emitting of the output signal by the emitting device; and determine, based on the sensor data, a quality metric for an optical measurement performed or to be performed by an optical measurement device included in the hearing device.

To illustrate, the optical measurement device may include at least one light source configured to emit light and at least one photodetector for detecting a reflected and/or scattered part of the light. When the hearing device is worn at the ear of the user, the optical measurement device of the hearing device may be positioned within an ear canal of the user (e.g., in contact with and/or with uniform pressure against the skin of the ear canal) to perform an optical measurement of the user. For example, the light source of the optical measurement device may be configured to emit the light into skin or tissue at the ear canal and the photodetector may be configured to detect part of the emitted light scattered by the skin or tissue. Optical detector data, based on the detected light, may be outputted by the optical measurement device for use in determining the optical measurement. E.g., the detector data may be indicative of a blood property of the user such as a heart rate, a blood pressure, a heart rate variability, an oxygen saturation index (SpO2), a maximum rate of oxygen consumption (VO2max), and/or a concentration of an analyte contained in the tissue, such as water and/or glucose.

The system described herein may be used to determine whether the optical measurement device included in the hearing device is sufficiently positioned within the ear canal to perform a quality optical measurement (e.g., to allow the light source of the optical measurement device to emit the light into skin or tissue at the ear canal and/or to allow the photodetector to detect part of the emitted light scattered by the skin or tissue). For example, the output signal emitted inside the ear canal by the emitting device may be attenuated or blocked by the hearing device seated in the ear canal so that the sensor outside the ear canal may detect a strongly attenuated output signal or no output signal at all. This may confirm that the hearing device is properly positioned at the ear of the user, which may result in the optical measurement device being properly positioned in the ear canal to perform a quality optical measurement. In case the hearing device is not properly seated in the ear canal (which, by extension, may indicate that the measurement device is also not properly positioned to perform a quality measurement), attenuation of the output signal may be comparatively weak and a comparatively strong signal may be detected by the external senor outside the ear.

The output signal emitted inside the ear canal by the emitting device may be an acoustic signal or an optical signal. The sensor outside the ear canal may be an acoustic sensor or an optical sensor, respectively. The sensor outside the ear canal may be positioned and configured such that it is able to detect the output signal emitted inside the ear canal which exits the ear canal, i.e. is not blocked by the hearing device. In particular in the case of a sensor outside the ear canal which is integrated into the hearing device, the sensor is positioned and configured in the hearing device in such a manner that it is able to detect the output signal exiting the ear canal or, in other words, leaking from the ear canal at an interface between the hearing device and the ear canal. This may in particular mean that a sensitive area of the sensor may be positioned and configured to face an outside portion at an interface between the hearing device and the ear canal.

The principles described herein may result in improved hearing systems compared to conventional systems that are not configured to determine a quality metric for an optical measurement based on placement of a hearing device, as well as provide other benefits as described herein. For example, a hearing system configured to determine a quality metric for an optical measurement based on placement of the hearing device may indicate an accuracy level of the optical measurement performed or to be performed by the optical measurement device included in the hearing device. The hearing system may further improve the accuracy level of the optical measurement (e.g., by prompting the user to reposition the hearing device and/or optical measurement device). Moreover, a hearing system configured to determine a quality metric for an optical measurement based on placement of the hearing device may allow the hearing system to be more computationally efficient by adjusting one or more settings of the hearing system and/or performing other operations. For example, the hearing system may abstain from taking the optical measurement and/or disable the optical measurement device.

Various embodiments will now be described in more detail with reference to the figures. The systems, hearing devices, and methods described herein may provide one or more of the benefits mentioned above and/or various additional and/or alternative benefits that will be made apparent herein. While embodiments for a hearing system configured to determine a quality metric for an optical measurement are described below, the described embodiments may further be configured to determine a quality metric for other measurements of user conditions (e.g., respiratory, temperature, etc.) that may be affected by displacement of a measurement device included in the hearing device.

Figure 1:
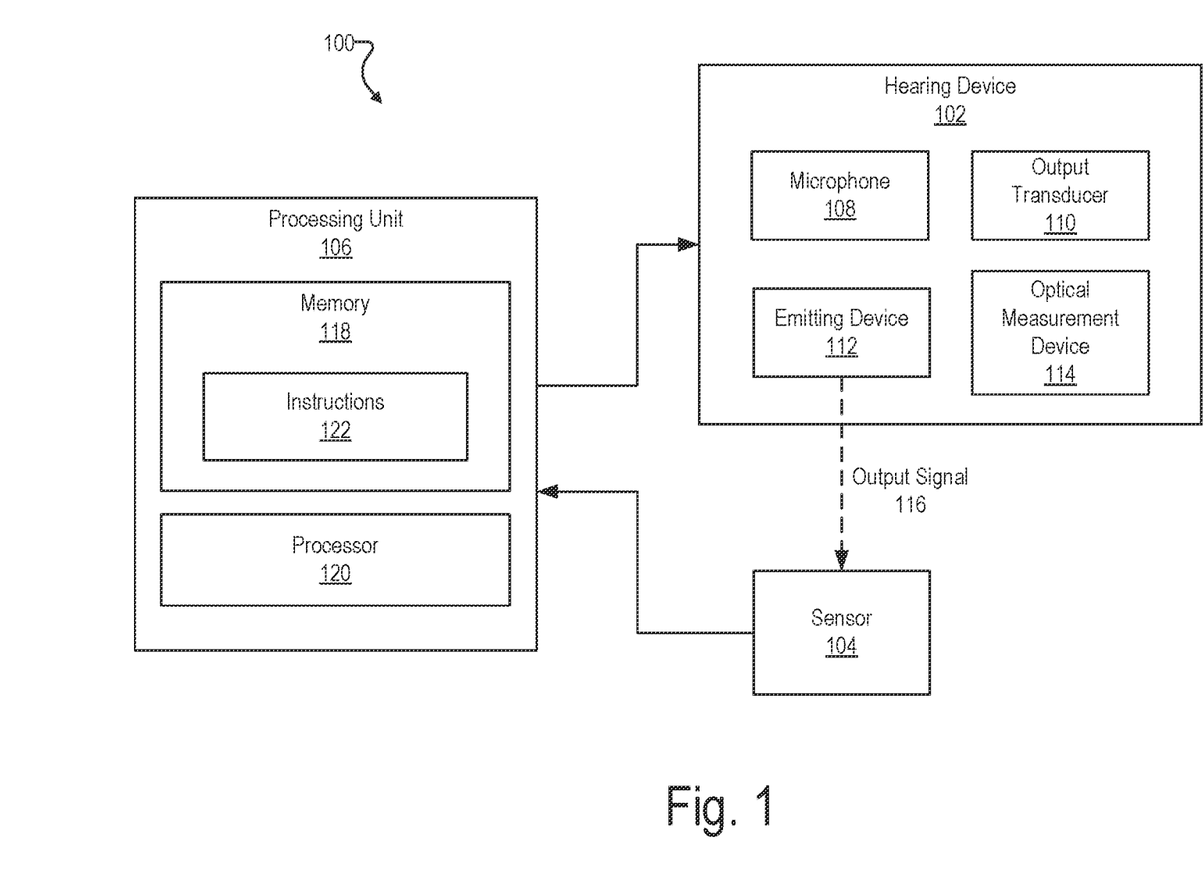
FIG. 1 shows an illustrative implementation of a hearing system.

FIG. 1 shows an illustrative implementation 100 of a hearing system configured to determine a quality metric for an optical measurement based on a position of an optical measurement device included in a hearing device configured to be worn by a user. For example, the optical measurement device included in the hearing device may be positioned within an ear canal of the user (e.g., in contact with and/or with uniform pressure against the skin of the ear canal) when the hearing device is worn as intended by the user to allow the optical measurement device to perform an optical measurement. As shown, implementation 100 includes a hearing device 102 and a sensor 104 communicatively coupled with a processing unit 106. Implementation 100 may include additional or alternative components as may serve a particular implementation.

Hearing device 102 herein is to be understood as any device outputting sound to a user that includes components that are worn at least partially in an ear canal of a user. In particular, hearing device 102 may be implemented as a hearing aid or a hearing instrument configured to enable or enhance hearing by a user wearing hearing device 102. For example, hearing device 102 may be implemented by a hearing aid configured to provide an amplified version of audio content to a user, a sound processor included in a cochlear implant system configured to provide electrical stimulation representative of audio content to a user, a sound processor included in a bimodal hearing system configured to provide both amplification and electrical stimulation representative of audio content to a user, or any other suitable hearing prosthesis. As described herein, hearing device 102 may include one or more components configured to be at least partially positioned within an ear canal of the user. For example, hearing device 102 may be implemented by earbuds, earphones, hearables, and/or hearing instruments such as a Receiver-In-Canal (RIC) device, an In-The-Ear (ITE) device, a Completely-In-Canal (CIC) device, and/or an Invisible-In-The-Canal (IIC) device.

As shown, hearing device 102 includes a microphone 108, an output transducer 110, an emitting device 112, and an optical measurement device 114. Hearing device 102 may include additional or alternative components as may serve a particular implementation.

Microphone 108 may be implemented by one or more suitable audio detection devices configured to detect an audio signal presented to a user of hearing device 102. In particular, microphone 108 may include an electro acoustic transducer configured to convert an audio signal in the form of an acoustic signal, e.g. sound, into an electric audio signal, i.e. an electric signal comprising information representative of the acoustic signal. The audio signal may include, for example, audio content (e.g., music, speech, noise, etc.) generated by one or more audio sources included in an environment of the user. Microphone 108 may be included in or communicatively coupled to hearing device 102 in any suitable manner. In some implementations, an interface may be included in addition to or instead of microphone 108 to receive an audio stream such as an electrical audio signal from a streaming source (e.g., a table microphone and/or a streaming service). Output transducer 110 may be implemented by any suitable audio output device, for instance a loudspeaker, also called 'receiver', of a hearing device or an output electrode of a cochlear implant system.

Emitting device 112 may be implemented by one or more suitable output devices configured to emit an output signal 116 that may be detected by sensor 104. For example, emitting device 112 may be configured to emit an audio signal (e.g., noise, random noise, pseudo-random noise, maximum length sequence, a temporally and/or spectrally patterned signal, frequency sweep, etc.), an optical signal (e.g., infrared, green light, etc.), and/or any other suitable signal that may be detected by sensor 104. Emitting device 112 may be positioned within an ear canal of the user while hearing device 102 is being worn by the user. Emitting device 112 may be included in or communicatively coupled to hearing device 102 in any suitable manner. In some implementations, emitting device 112 may be part of optical measurement device 114 and/or output transducer 110.

Sensor 104 may be implemented by one or more suitable detection devices configured to attempt to detect output signal 116 and output sensor data representative of one or more signals detected by sensor 104 during a time period corresponding to the emitting of output signal 116 by emitting device 112. For example, sensor 104 may include an acoustic sensor (e.g., a microphone, etc.), an optical sensor (e.g., photodetector, etc.) and/or any other suitable sensor to attempt to detect output signal 116. Sensor 104 may be positioned outside of an ear canal of the user and facing at least a portion at an outside interface between hearing device 102 and the ear canal. In some implementations, sensor 104 is included in a different wearable device separate from hearing device 102 (e.g., a watch or a mobile device worn or carried by the user). In instances where sensor 104 is included in a different wearable device, an additional metric may be provided that is indicative of proper positioning of sensor 104. For example, sensor 104 may be positioned to attempt to detect output signal 116 without or with little leakage due to positioning of sensor 104 (e.g., if sensor 104 is positioned at a distance too far away from emitting device 112, if sensor 104 is blocked, etc.). The positioning of sensor 104 may be measured by magnetic reference points, optical detection, a proximal sensor, etc. In these alternative configurations, hearing device 102 may access output sensor data generated by sensor 104 by being communicatively coupled to the different device. E.g., sensor 104 may be coupled to processing unit 106 so that output sensor data may be processed. Alternatively, sensor 104 may be included in hearing device 102 (see also FIG. 2).

Optical measurement device 114 may be implemented by any suitable device configured to perform an optical measurement of a condition of the user and output data representative of the optical measurement. For example, optical measurement device 114 may include at least one light source or emitting device configured to emit light and at least one photodetector or optical sensor configured to detect part of the emitted light reflected and/or scattered by the skin of the user. In some examples, optical measurement device 114 may be implemented by a photoplethysmography (PPG) sensor. Output data may be provided by the PPG sensor as a PPG waveform, which may be indicative of a blood property, such as a heart rate, a blood pressure, a heart rate variability, an oxygen saturation index (SpO2), a maximum rate of oxygen consumption (VO2max), and/or a concentration of an analyte contained in the tissue, such as water and/or glucose. In some implementations, optical measurement device 114 is included in hearing device 102 to position at least a portion of optical measurement device 114 within an ear canal of the user for generating output data. For example, optical measurement device 114 may be sufficiently positioned within the ear canal (e.g., in contact with and/or with uniform pressure against the skin of the ear canal) to allow the light source of the optical measurement device to emit the light into skin or tissue at the ear canal and/or to allow the photodetector to detect part of the emitted light scattered by the skin or tissue.

Processing unit 106 may be implemented by one or more computing devices and/or computer resources (e.g., processors, memory devices, storage devices, etc.) as may serve a particular implementation. For example, processing unit 106 may be implemented by a mobile device, personal computer, and/or other computing device configured to be communicatively coupled (e.g., by way of a wired and/or wireless connection) to hearing device 102. As shown, processing unit 106 may include, without limitation, a memory 118 and a processor 120 selectively and communicatively coupled to one another. Memory 118 and processor 120 may each include or be implemented by computer hardware that is configured to store and/or process computer software. Various other components of computer hardware and/or software not explicitly shown in FIG. 1 may also be included within processing unit 106. In some examples, memory 118 and/or processor 120 may be distributed between multiple devices and/or multiple locations as may serve a particular implementation.

Memory 118 may store and/or otherwise maintain executable data used by processor 120 to perform any of the functionality described herein. For example, memory 118 may store instructions 122 that may be executed by processor 120. Memory 118 may be implemented by one or more memory or storage devices, including any memory or storage devices described herein, that are configured to store data in a transitory or non-transitory manner. Instructions 122 may be executed by processor 120 to cause processing unit 106 to perform any of the functionality described herein. Instructions 122 may be implemented by any suitable application, software, code, and/or other executable data instance. Additionally, memory 118 may also maintain any other data accessed, managed, used, and/or transmitted by processor 120 in a particular implementation.

Processor 120 may be implemented by one or more computer processing devices, including general purpose processors (e.g., central processing units (CPUs), graphics processing units (GPUs), microprocessors, etc.), special purpose processors (e.g., application specific integrated circuits (ASICs), field-programmable gate arrays (FPGAs), etc.), image signal processors, or the like. Using processor 120 (e.g., when processor 120 is directed to perform operations represented by instructions 122 stored in memory 118), processor 120 may perform various operations as described herein.

Figure 2:
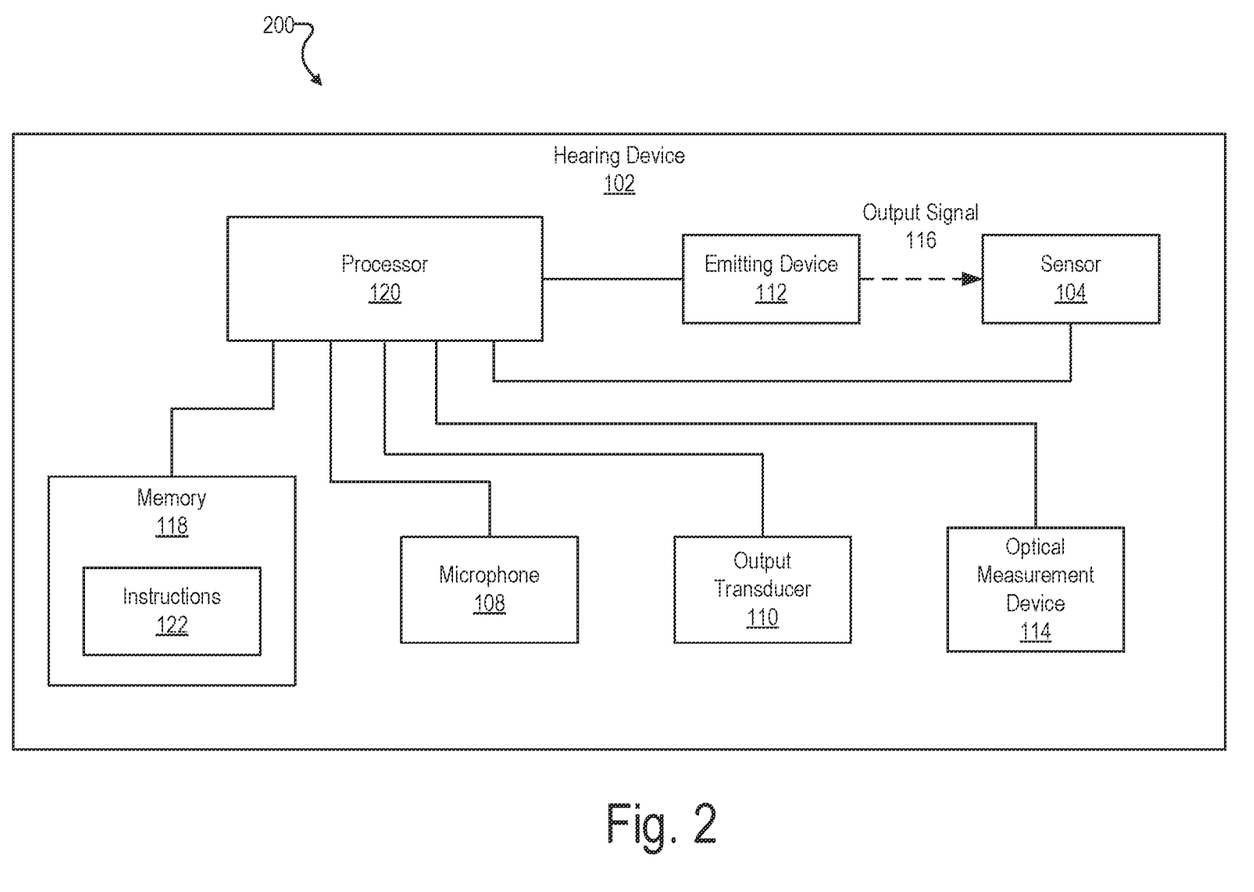
FIG. 2 shows another illustrative implementation of a hearing system.

FIG. 2 shows another illustrative implementation 200 of a hearing system configured to determine a quality metric for an optical measurement based on a position of an optical measurement device included in a hearing device configured to be worn by a user. As shown, implementation 200 is similar to implementation 100, except that implementation 200 includes sensor 104, processor 120, and memory 118 located within hearing device 102. Implementation 200 may include additional or alternative components as may serve a particular implementation. For example, in instances where emitting device 112 is configured to output an audio signal, emitting device 112 may be implemented by output transducer 110 and/or sensor 104 may be implemented by microphone 108. Alternatively, in instances where emitting device 112 is configured to output an optical signal, emitting device 112 may be implemented by the light source of optical measurement device 114.

Figure 3:
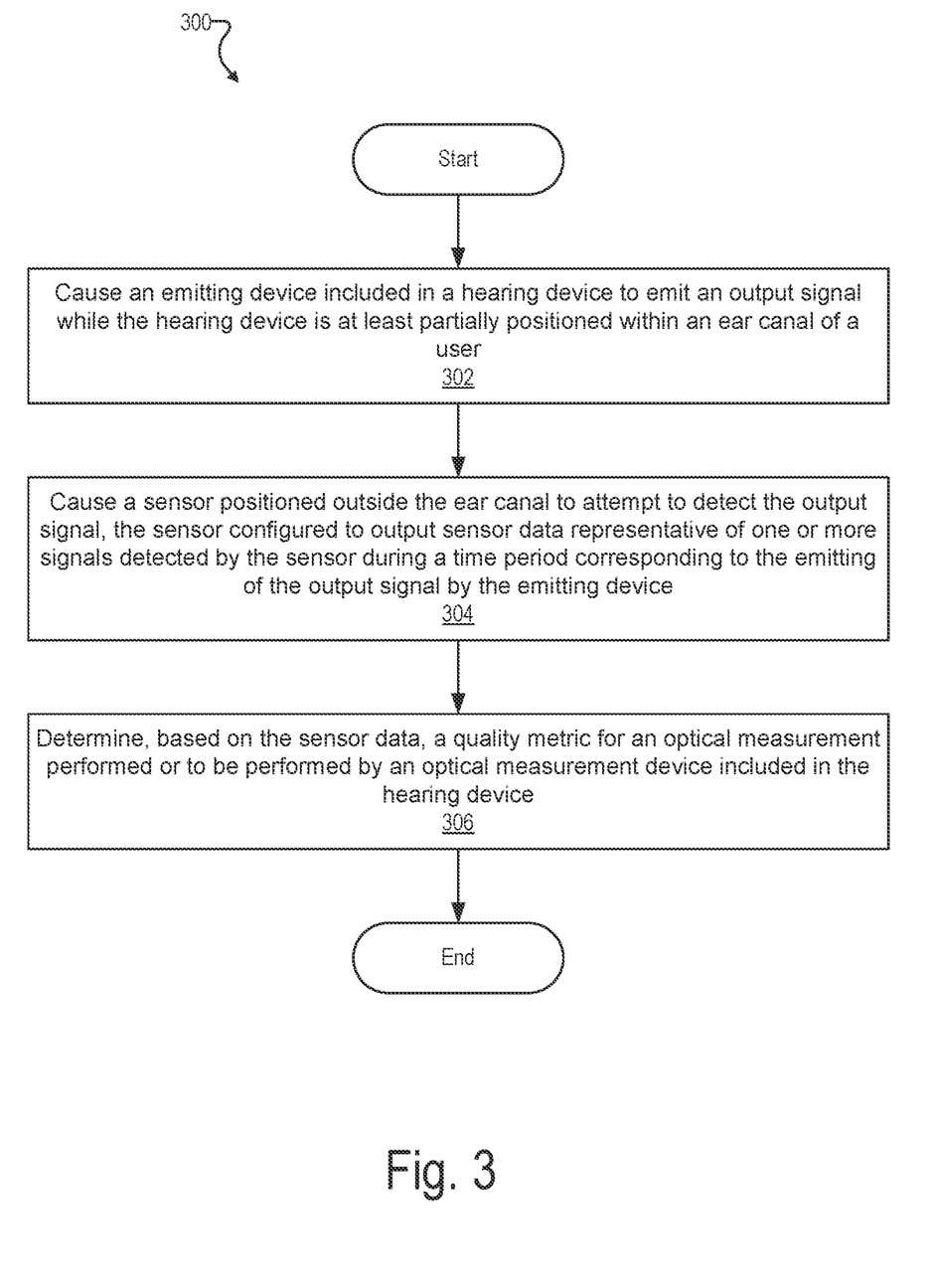
FIG. 3 shows an illustrative method of operating a hearing system.

FIG. 3 shows an illustrative method 300 that may be performed by a hearing system according to the principles described herein. While FIG. 3 illustrates exemplary operations according to one embodiment, other embodiments may omit, add to, reorder, and/or modify any of the operations shown in FIG. 3. Moreover, each of the operations depicted in FIG. 3 may be performed in any of the ways described herein.

As shown, a hearing system may, at operation 302, cause emitting device 112 included in hearing device 102 to emit output signal 116 while hearing device 102 is at least partially positioned within an ear canal of a user. The hearing system may, at operation 304, cause sensor 104 positioned outside the ear canal to attempt to detect output signal 116. In some implementations, the hearing system may be configured to cause sensor 104 to output sensor data representative of one or more signals detected by sensor 104 during a time period corresponding to the emitting of output signal 116 by emitting device 112, The hearing system may, at operation 306, determine, based on the sensor data, a quality metric for an optical measurement performed or to be performed by optical measurement device 114 included in hearing device 102.

Figure 4:
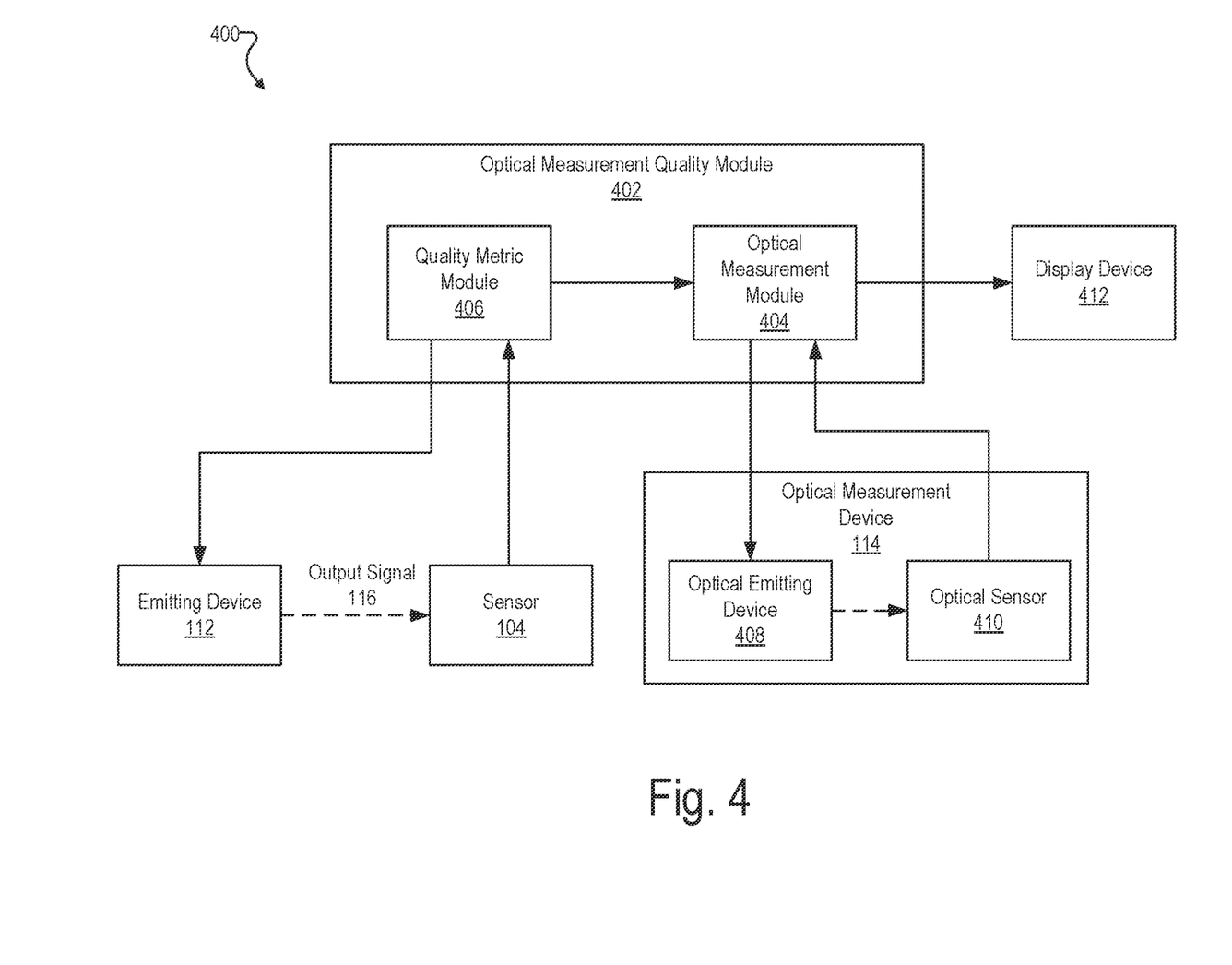
FIG. 4 shows an illustrative implementation of an optical measurement quality determination module that may be incorporated into a hearing system.

As an illustrative example. FIG. 4 shows an implementation 400 of an optical measurement quality module 402 that may be implemented by a hearing system (e.g., by processor 120) according to the principles described herein and configured to determine a quality metric for an optical measurement. As shown, optical measurement quality module 402 may include an optical measurement module 404 and a quality metric module 406. Optical measurement quality module 402 may include additional or alternative components as may serve a particular implementation.

Optical measurement module 404 may be communicatively coupled (e.g., by way of a wired and/or wireless connection) to optical measurement device 114 and configured to determine an optical measurement performed by optical measurement device 114. For example, optical measurement module 404 may be configured to cause an optical emitting device 408 of optical measurement device 114 to emit an optical signal (e.g., infrared, green light, etc.) and to cause an optical sensor 410 of optical measurement device 114 to attempt to detect the optical signal (e,g., during a time period corresponding to the emitting of the optical signal by optical emitting device 408, such as up to about 30 seconds, up to about 10 seconds, and/or up to about 2 seconds). Optical measurement module 404 may further be configured to receive optical sensor data representative of one or more signals detected by optical sensor 410 and outputted by optical sensor 410. Optical measurement module 404 may be configured to process the optical sensor data to determine an optical measurement of a condition of the user. For example, optical measurement module 404 may be configured to determine a heart rate of the user based on the optical sensor data. In some implementations, optical measurement module 404 may further be configured to output the optical measurement to a display device 412 (e.g., a watch, mobile device, etc.) to display the optical measurement to the user.

Quality metric module 406 may be configured to determine a quality metric for the optical measurement performed or to be performed by optical measurement device 114. For example, quality metric module 406 may be communicatively coupled (e.g., by way of a wired and/or wireless connection) to emitting device 112 and may be configured to cause emitting device 112 to emit output signal 116. Quality metric module 406 may cause output signal 116 to be emitted continuously or periodically based on an amount of time that has elapsed since a previously emitted output signal 116 (e.g., up to about 60 minutes, up to about 30 minutes, and/or up to about 5 minutes). In some implementations, quality metric module 406 may be configured to cause emitting device 112 to emit output signal 116 based on an event associated with hearing device 102 (e.g., when hearing device 102 is powered on, when hearing device 102 is positioned within an ear of the user, etc.) and/or based on a user input received from a user interface. For example, quality metric module 406 may be communicatively coupled (e.g., by way of a wired and/or wireless connection) with a user interface included in hearing device 102 and/or different wearable device separate from hearing device 102 (e.g., a watch or a mobile device worn or carried by the user) to receive a user input from the user interface, Still other suitable configurations and/or methods for causing emitting device 112 to emit output signal 116 may be used.

Quality metric module 406 may further be communicatively coupled (e.g., by way of a wired and/or wireless connection) to sensor 104. Quality metric module 406 may be configured to cause sensor 104 to attempt to detect output signal 116 (e.g., during a time period corresponding to the emitting of output signal 116 by emitting device 112) and receive output sensor data generated by sensor 104.

Quality metric module 406 may process the sensor data to determine the quality metric for the optical measurement performed or to be performed by optical measurement device 114. The quality metric may be represented by any suitable metric, such as a discrete value (e.g., a percentage, a level, a range, a probability value, etc.) representative of a quality level of the optical measurement performed or to be performed by optical measurement device 114. In some implementations, a quality metric having a higher value within a given range, e.g. between 1 to 100 (e.g., greater than about 50, greater than about 75, and/or greater than about 90), may indicate a proper position of optical measurement device 114 for performing an optical measurement. Alternatively, a quality metric having a lower value (e.g., less than about 49, less than about 25, and/or less than about 10) may indicate that optical measurement device 114 is displaced or not positioned properly for performing an optical measurement.

In some implementations, quality metric module 406 may determine the quality metric by comparing the sensor data generated by sensor 104 with reference data representative of a predetermined level for sensor data. Such reference data may be based on previous levels of sensor data and/or a level of output signal 116 emitted by emitting device 112. In some examples, the reference data may be stored in memory 118. The reference data may be input by the user and/or a hearing care professional (e.g., when fitting hearing device 102 to the user). For example, the user and/or hearing care professional may confirm proper positioning of hearing device 102 in a controlled environment to input, generate, calibrate and/or save reference data for a specific user and/or wearing situation. In some instances, the reference data may include a zero detection (e.g., in instances when hearing device 102 blocks output signal 116). Quality metric module 406 may determine the quality metric based on how closely the sensor data corresponds to the reference data.

As an illustrative example, when hearing device 102 is properly positioned at the ear, hearing device 102 may block or strongly attenuate output signal 116 emitted by emitting device 112 within the ear canal. In these instances, sensor 104, positioned outside the ear canal, may detect no output signal 116 (e.g., when hearing device 102 seals the ear canal to block output signal 116 from exiting the ear canal) or a low level of output signal 116 emitted by emitting device 112 (e.g., not exceeding about 50% of the original intensity of output signal 116, not exceeding about 20% of the original intensity of output signal 116, and/or not exceeding about 10% of the original intensity of output signal 116). When hearing device 102 is properly positioned, optical measurement device 114 is also adequately positioned on the user to perform an optical measurement. In such instances, quality metric module 406 may increase the quality metric. Alternatively, sensor 104 may detect a high level of output signal 116 when hearing device 102 is displaced within an ear of the user, i.e. the hearing device 102 is not properly positioned in the ear canal (e.g., exceeding about 50% of the original intensity of output signal 116, exceeding about 80% of the original intensity of output signal 116, and/or exceeding about 90% of the original intensity of output signal 116). This may indicate that optical measurement device 114 is also displaced, which may degrade the accuracy of the optical measurement performed or to be performed by optical measurement device 114, In such instances, quality metric module 406 may decrease the quality metric. Still other suitable configurations and/or methods for determining the quality metric may be used. In some implementations, quality metric module 406 may be configured to cause display device 412 to display the quality metric to the user (e.g., in combination with the optical measurement corresponding to the quality metric).

Quality metric module 406 may further be configured to perform, based on the quality metric, an operation with respect to hearing device 102. In some implementations, when the quality metric is less than a threshold, quality metric module 406 may be configured to prompt the user to reposition hearing device 102. For example, quality metric module 406 may cause display device 412 to display a prompt to the user to reposition hearing device 102. Additionally or alternatively, quality metric module 406 may prompt the user to reposition hearing device 102 by causing a sound (e.g., a beep, a recording, a voice message, etc.) to be emitted and/or a light (e.g., a light-emitting diode (LED))

to be illuminated on hearing device 102 and/or a separate device worn or carried by the user (e.g., a watch, a mobile phone, etc.). Still other suitable methods for prompting the user to reposition hearing device 102 when the quality metric is below a threshold may be used.

As another example, when the quality metric is less than a threshold, quality metric module 406 may be configured to discard the optical measurement performed by optical measurement device 114 and/or abstain from taking the optical measurement to be performed by optical measurement device 114. In some implementations, quality metric module 406 may discard the optical measurement and/or abstain from taking the optical measurement if the user fails to reposition hearing device 102 for a period of time after receiving a prompt to reposition hearing device 102. Alternatively, when the quality metric is less than a threshold, quality metric module 406 may be configured to disable optical measurement device 114.

Figure 5:
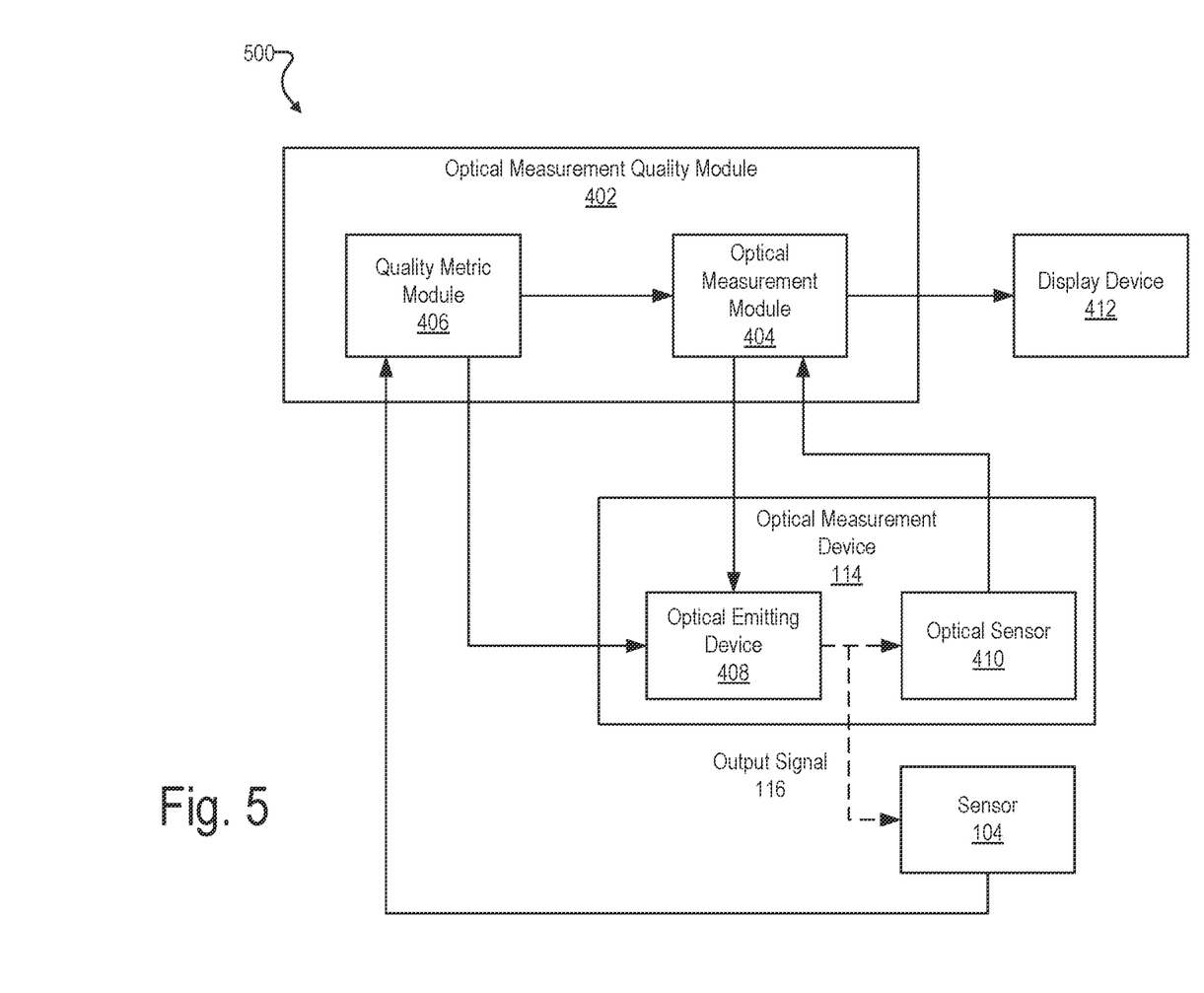
FIG. 5 shows another illustrative implementation of an optical measurement quality determination module that may be incorporated into a hearing system.

FIG. 5 shows another illustrative implementation 500 of optical measurement quality module 402 to determine a quality metric for an optical measurement. As shown, implementation 500 is similar to implementation 400, except that emitting device 112 has been omitted such that optical emitting device 408 of optical measurement device 114 may be configured to emit output signal 116 instead of emitting device 112. Implementation 500 may include additional or alternative components as may serve a particular implementation.

In certain embodiments, one or more of the processes described herein may be implemented at least in part as instructions embodied in a non-transitory computer-readable medium and executable by one or more computing devices. In general, a processor (e.g., a microprocessor) receives instructions, from a non-transitory computer-readable medium, (e.g., a memory, etc.), and executes those instructions, thereby performing one or more processes, including one or more of the processes described herein. Such instructions may be stored and/or transmitted using any of a variety of known computer-readable media.

A computer-readable medium (also referred to as a processor-readable medium) includes any non-transitory medium that participates in providing data (e.g., instructions) that may be read by a computer (e.g., by a processor of a computer). Such a medium may take many forms, including, but not limited to, non-volatile media, and/or volatile media. Non-volatile media may include, for example, optical or magnetic disks and other persistent memory. Volatile media may include, for example, dynamic random access memory ("DRAM"), which typically constitutes a main memory. Common forms of computer-readable media include, for example, a disk, hard disk, magnetic tape, any other magnetic medium, a compact disc read-only memory ("CD-ROM"), a digital video disc ("DVD"), any other optical medium, random access memory ("RAM"), programmable read-only memory ("PROM"), electrically erasable programmable read-only memory ("EPROM"), FLASH-EEPROM, any other memory chip or cartridge, or any other tangible medium from which a computer can read.

Figure 6:
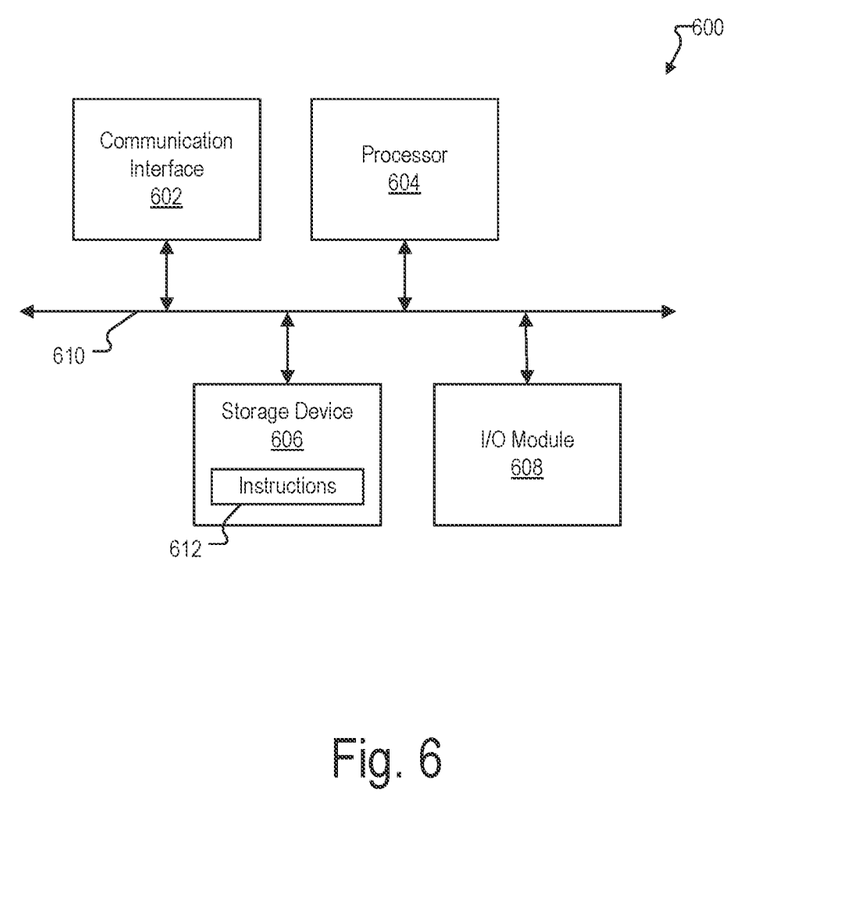
FIG. 6 shows an illustrative computing system according to the principles described herein.

FIG. 6 shows an illustrative computing device 600 that may be specifically configured to perform one or more of the processes described herein. Any of the systems, computing devices, and/or other components described herein may be implemented by computing device 600.

As shown in FIG. 6, computing device 600 may include a communication interface 602, a processor 604, a storage device 606, and an input/output ("I/O") module 608 communicatively connected one to another via a communication infrastructure 610. While an illustrative computing device 600 is shown in FIG. 6, the components illustrated in FIG. 6 are not intended to be limiting. Additional or alternative components may be used in other embodiments. Components of computing device 600 shown in FIG. 6 will now be described in additional detail.

Communication interface 602 may be configured to communicate with one or more computing devices. Examples of communication interface 602 include, without limitation, a wired network interface (such as a network interface card), a wireless network interface (such as a wireless network interface card), a modem, an audio/video connection, and any other suitable interface.

Processor 604 generally represents any type or form of processing unit capable of processing data and/or interpreting, executing, and/or directing execution of one or more of the instructions, processes, and/or operations described herein. Processor 604 may perform operations by executing computer-executable instructions 612 (e.g., an application, software, code, and/or other executable data instance) stored in storage device 606.

Storage device 606 may include one or more data storage media, devices, or configurations and may employ any type, form, and combination of data storage media and/or device. For example, storage device 606 may include, but is not limited to, any combination of the non-volatile media and/or volatile media described herein. Electronic data, including data described herein, may be temporarily and/or permanently stored in storage device 606. For example, data representative of computer-executable instructions 612 configured to direct processor 604 to perform any of the operations described herein may be stored within storage device 606. In some examples, data may be arranged in one or more databases residing within storage device 606.

I/O module 608 may include one or more I/O modules configured to receive user input and provide user output. I/O module 608 may include any hardware, firmware, software, or combination thereof supportive of input and output capabilities. For example, I/O module 608 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 608 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 608 is configured to provide graphical data to a display for presentation to a user. The graphical data may be representative of one or more graphical user interfaces and/or any other graphical content as may serve a particular implementation, In the preceding description, various exemplary embodiments have been described with reference to the accompanying drawings, It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
   a memory storing instructions; and a processor communicatively coupled to the memory and configured to execute the instructions to:
cause an emitting device included in a hearing device to emit an output signal while the hearing device is at least partially positioned within an ear canal of a user;
cause a sensor positioned outside the ear canal to attempt to detect the output signal, the sensor configured to output sensor data representative of one or more signals detected by the sensor during a time period corresponding to the emitting of the output signal by the emitting device; and
determine, based on the sensor data, a quality metric for an optical measurement performed or to be performed by an optical measurement device included in the hearing device.

2. The system of claim 1, wherein the output signal emitted by the emitting device is an acoustic signal and wherein the sensor comprises an acoustic sensor configured to attempt to detect the acoustic signal.

3. The system of claim 2, wherein the emitting device is provided by an output transducer of the hearing device and wherein the sensor is provided by a microphone of the hearing device.

4. The system of claim 1, wherein the output signal emitted by the emitting device is an optical signal and wherein the sensor comprises an optical sensor configured to attempt to detect the optical signal.

5. The system of claim 4, wherein the emitting device is provided by a light source of the optical measurement device and wherein the optical measurement device further comprises a photodetector configured to attempt to detect the optical signal to perform the optical measurement.

6. The system of claim 1, wherein the determining of the quality metric is based on attenuation of the output signal by the hearing device.

7. The system of claim 6, wherein the determining of the quality metric includes a select one or both of increasing the quality metric when the sensor detects a low level of the output signal or decreasing the quality metric when the sensor detects a high level of the output signal.

8. The system of claim 1, wherein the determining of the quality metric includes comparing the sensor data with reference data representative of a predetermined level for the sensor data.

9. The system of claim 1, wherein the processor is further configured to execute the instructions to perform, based on the quality metric, an operation with respect to the hearing device.

10. The system of claim 9, wherein when the quality metric is less than a threshold, the operation comprises one or more of: prompting the user to reposition the hearing device, discarding the optical measurement performed by the optical measurement device, abstaining from taking the optical measurement to be performed by the optical measurement device, and disabling the optical measurement device.

11. The system of claim 1, wherein the causing the emitting device to emit the output signal is based on one or more of: a user input received from a user interface, an event associated with the hearing device, or an amount of time that has elapsed since a previously emitted output signal.

12. A hearing device configured to be worn by a user, the hearing device comprising:
an emitting device configured to be positioned within an ear canal of the user;
a sensor configured to be positioned outside the ear canal;
an optical measurement device configured to be positioned within the ear canal; and
a processing unit communicatively coupled to the emitting device and the sensor, the processing unit configured to:
cause the emitting device to emit an output signal while the hearing device is at least partially positioned within the ear canal;
cause the sensor to attempt to detect the output signal, the sensor configured to output sensor data representative of one or more signals detected by the sensor during a time period corresponding to the emitted of the output signal by the emitting device; and
determine, based on the sensor data, a quality metric for an optical measurement performed or to be performed by the optical measurement device.

13. The hearing device of claim 12, wherein the emitting device is provided by an output transducer of the hearing device, the output transducer configured to emit an acoustic signal, and wherein the sensor is provided by a microphone of the hearing device, the microphone configured to attempt to detect the acoustic signal.

14. The hearing device of claim 12, wherein the emitting device is provided by a light source of the optical measurement device, the light source configured to emit an optical signal, and wherein the optical measurement device further comprises a photodetector configured to attempt to detect the optical signal to perform the optical measurement.

15. A method comprising:
causing, by at least one computing device, an emitting device included in a hearing device to emit an output signal while the hearing device is at least partially positioned within an ear canal of a user;
causing, by the at least one computing device, a sensor positioned outside the ear canal to attempt to detect the output signal, the sensor configured to output sensor data representative of one or more signals detected by the sensor during a time period corresponding to the emitting of the output signal by the emitting device; and
determining, by the at least one computing device based on the sensor data, a quality metric for an optical measurement performed or to be performed by an optical measurement device included in the hearing device.

16. The method of claim 15, wherein the output signal comprises a select one or both of an acoustic signal or an optical signal.

17. The method of claim 15, wherein the determining the quality metric is based on attenuation of the output signal by the hearing device.

18. The method of claim 17, wherein the determining the quality metric includes a select one or both of increasing the quality metric when the sensor detects a low level of the output signal or decreasing the quality metric when the sensor detects a high level of the output signal.

19. The method of claim 15, wherein the determining of the quality metric includes comparing the sensor data with reference data representative of a predetermined level for the sensor data.

20. The method of claim 15, further comprising performing, when the quality metric is less than a threshold, one or more of: prompting the user to reposition the hearing device, discarding the optical measurement performed by the optical measurement device, abstaining from taking the optical measurement to be performed by the optical measurement device, and disabling the optical measurement device.

* * * * *